US011006927B2

(12) United States Patent
Dufour et al.

(10) Patent No.: US 11,006,927 B2
(45) Date of Patent: May 18, 2021

(54) ULTRASOUND IMAGING APPARATUS

(71) Applicant: KONINKLIJKE PHILIPS N.V., Eindhoven (NL)

(72) Inventors: Cecile Dufour, Eindhoven (NL); Stephane Allaire, Eindhoven (NL); Oudom Somphone, Eindhoven (NL); Vijay Thakur Shamdasani, Eindhoven (NL); Gary Cheng-How Ng, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 546 days.

(21) Appl. No.: 15/561,264

(22) PCT Filed: Mar. 31, 2016

(86) PCT No.: PCT/EP2016/057044
§ 371 (c)(1),
(2) Date: Sep. 25, 2017

(87) PCT Pub. No.: WO2016/156481
PCT Pub. Date: Oct. 6, 2016

(65) Prior Publication Data
US 2018/0116635 A1  May 3, 2018

Related U.S. Application Data

(60) Provisional application No. 62/140,718, filed on Mar. 31, 2015.

(30) Foreign Application Priority Data

Apr. 14, 2015 (EP) .................................... 15163507

(51) Int. Cl.
*A61B 8/08* (2006.01)
*G01S 7/52* (2006.01)
(Continued)

(52) U.S. Cl.
CPC .............. *A61B 8/483* (2013.01); *A61B 8/461* (2013.01); *A61B 8/523* (2013.01); *A61B 8/5207* (2013.01);
(Continued)

(58) Field of Classification Search
CPC ....... A61B 8/0883; A61B 8/461; A61B 8/463; A61B 8/467; A61B 8/483; A61B 8/5207;
(Continued)

(56) References Cited

U.S. PATENT DOCUMENTS 6,241,675 B1   6/2001  Smith et al.
6,306,091 B1 * 10/2001  Sunnanaweera .... G01S 7/52023
                                                                    128/916

(Continued)

OTHER PUBLICATIONS

De Isla et al "Three Dimensional Wall Motion Tracking: A New and Faster Tool for Myocardial Strain . . . " Journal of the American Soc. of Echocardiography, vol. 22, No. 4 Apr. 1, 2009 p. 325-330.

*Primary Examiner* — Katherine L Fernandez

(57) ABSTRACT

An ultrasound imaging apparatus (16) is disclosed for providing two-dimensional ultrasound images of a patient. The ultrasound imaging apparatus comprises an input interface (18) for receiving three-dimensional ultrasound data of a volume of the patient from an ultrasound acquisition unit as a continuous data stream and a motion detection unit (22) for determining a motion of an object in the three-dimensional ultrasound data and a direction of the motion in the three-dimensional ultrasound data. An image processing unit (20) determines a spatial rotation angle (46) of an image plane (32, 34) within the volume on the basis of the determined direction of the motion and determines two-dimensional ultrasound image data on the basis of the three-dimensional ultrasound data in the image plane within the volume. The two-dimensional image data is provided via an output interface to a display unit (26).

13 Claims, 4 Drawing Sheets

(51) Int. Cl.

| | | |
|---|---|---|
| *G01S 15/89* | (2006.01) | |
| *G06T 7/70* | (2017.01) | |
| *A61B 8/00* | (2006.01) | |
| *G06T 7/00* | (2017.01) | |
| *G06T 7/20* | (2017.01) | |

(52) U.S. Cl.
CPC ........ *A61B 8/5223* (2013.01); *G01S 7/52074* (2013.01); *G01S 15/8984* (2013.01); *G01S 15/8993* (2013.01); *G06T 7/0012* (2013.01); *G06T 7/20* (2013.01); *G06T 7/70* (2017.01); *A61B 8/0883* (2013.01); *A61B 8/463* (2013.01); *A61B 8/467* (2013.01); *G06T 2207/10132* (2013.01); *G06T 2219/008* (2013.01)

(58) Field of Classification Search
CPC ... A61B 8/5223; A61B 8/523; G01S 15/8984; G01S 15/8993; G01S 7/52074; G06T 2207/10132; G06T 2219/008; G06T 7/0012; G06T 7/20; G06T 7/70
See application file for complete search history.

(56) References Cited

U.S. PATENT DOCUMENTS

| | | | |
|---|---|---|---|
| 6,589,176 B2 | 6/2003 | Jago et al. | |
| 8,480,583 B2 | 7/2013 | Lundberg | |
| 8,565,504 B2 | 10/2013 | Abe et al. | |
| 2005/0096538 A1* | 5/2005 | Chomas | A61B 8/14 600/437 |
| 2008/0009722 A1 | 1/2008 | Simopoulos et al. | |
| 2008/0221446 A1* | 9/2008 | Washburn | A61B 8/00 600/437 |
| 2008/0267482 A1 | 10/2008 | Abe et al. | |
| 2008/0294049 A1* | 11/2008 | Guracar | G06T 7/248 600/458 |
| 2009/0060306 A1* | 3/2009 | Ohuchi | A61B 8/14 382/131 |
| 2011/0079082 A1* | 4/2011 | Yoo | G01S 15/8993 73/632 |
| 2011/0144499 A1 | 6/2011 | Yoo et al. | |
| 2014/0013849 A1* | 1/2014 | Gerard | G01S 7/52084 73/602 |
| 2014/0163380 A1 | 6/2014 | Lee et al. | |
| 2016/0249885 A1* | 9/2016 | Schneider | A61B 8/523 382/131 |

* cited by examiner

ULTRASOUND IMAGING APPARATUS

This application is the U.S. National Phase application under 35 U.S.C. § 371 of International Application No. PCT/EP2016/057044, filed on Mar. 31, 2016, which claims the benefit of U.S. Provisional Application Ser. No. 62/140,718, filed Mar. 31, 2015 and EP Application Ser. No. 15163507.5 filed Apr. 14, 2015. These applications are hereby incorporated by reference herein.

FIELD OF THE INVENTION

The present invention relates to an ultrasound imaging apparatus for providing two-dimensional ultrasound images of the patient. The present invention further relates to an ultrasound imaging system. The present invention further relates to an ultrasound image evaluation method for providing two-dimensional ultrasound images of a patient and a computer program comprising program code means for causing a computer to carry out the steps of the method for providing the two-dimensional ultrasound images of the patient.

BACKGROUND OF THE INVENTION

In the field of ultrasound imaging systems, it is generally known to capture three-dimensional ultrasound image data from a volume of a patient and to derive two-dimensional ultrasound images from the three-dimensional ultrasound data in an image plane in order to display two-dimensional ultrasound images on a display screen. The two-dimensional ultrasound images derived from the three-dimensional ultrasound data can be determined in three different spatial image planes which are oriented orthogonal to each other.

It is further known to capture the three-dimensional ultrasound data from the patient in real time as a sequence of three-dimensional frames in order to provide a real time image of the patient including a motion of objects in the field of view in real time.

The image planes can be determined electronically in the ultrasound system and the two-dimensional images can be derived electronically from the three-dimensional ultrasound data having different spatial orientations corresponding to the position of the ultrasound probe in order to provide a certain image or view on certain organs of the patient. A corresponding system is e.g. known from EP 2 335 596 A1, wherein the image planes are determined as two-dimensional slices through the three-dimensional ultrasound data on the basis of the position of the ultrasound probe, which is detected by means of a position detecting unit.

The disadvantage of the known ultrasound image systems is that the image planes are determined on the basis of the probe position and the probe steering direction so that any image plane depends on the ultrasound probe position and the viewing direction and that the visualization of a dynamic behavior in the two-dimensional ultrasound images is complicated.

SUMMARY OF THE INVENTION

It is therefore an object of the invention to provide an improved ultrasound imaging apparatus and a corresponding improved ultrasound image evaluation method for providing two-dimensional ultrasound images of a patient, which can visualize certain features, in particular a dynamic behavior precisely with reduced handling effort for the user. According to one aspect of the present invention, an ultrasound imaging apparatus is provided for providing two-dimensional ultrasound images of a patient, comprising:

an input interface for receiving three-dimensional ultrasound data of a volume of the patient from an ultrasound acquisition unit as a continuous data stream, a motion detection unit for determining a motion of an object in the three-dimensional ultrasound data and a direction of the motion in the three-dimensional ultrasound data, an image processing unit for determining a spatial rotation angle of an image plane within the volume on the basis of the determined direction of the motion and for determining two-dimensional ultrasound image data on the basis of the three-dimensional ultrasound data in the image plane within the volume, and an output interface for providing the two-dimensional image data to a display unit.

According to another aspect of the present invention, an ultrasound imaging system is provided comprising:

an ultrasound acquisition unit including an ultrasound probe for acquiring three-dimensional ultrasound data of the volume of a patient, a display unit for displaying ultrasound image data on the basis of the three-dimensional ultrasound data, and an ultrasound imaging apparatus according to the present invention for determining the ultrasound image data to be displayed on the display unit.

According to another aspect of the present invention, an ultrasound image evaluation method is provided for providing two-dimensional ultrasound images of a patient, comprising the steps of:

receiving three-dimensional ultrasound data of a volume of a patient as a continuous data stream, determining a motion of an object within the three-dimensional ultrasound data and a direction of the motion in the three-dimensional ultrasound data, determining a spatial rotation angle for an image plane within the volume on the basis of the determined direction of the motion, determining the image plane within the volume on the basis of the spatial rotation angle and determining the two-dimensional ultrasound images on the basis of the three-dimensional ultrasound data in the image plane, and providing the two-dimensional image data to a display unit.

According to still another aspect of the present invention, a computer program is provided comprising program code means for causing a computer to carry out the steps of the ultrasound image evaluation method according to the present invention, when said computer program is carried out on a computer.

Preferred embodiments of the invention are defined in the dependent claims. It shall be understood that the claimed method has similar and/or identical preferred embodiments as the claimed device and as defined in the dependent claims.

The present invention is based on the idea to determine a motion of an object in the three-dimensional ultrasound data and to determine a direction of the motion in the three-dimensional ultrasound data and to determine a spatial rotation angle or a spatial orientation of an image plane in the three-dimensional ultrasound data on the basis of the direction of the motion determined in the three-dimensional ultrasound data. The two-dimensional image data is determined in the image plane so that the two-dimensional images displayed by the display unit are aligned to the motion of the object or the organ of the patient so that the visualization of the dynamic behavior in the three-dimensional ultrasound data is improved.

It shall be understood that the spatial rotation angle of the image plane may be determined initially on the basis of the motion detected in the three-dimensional ultrasound data or that the spatial rotation angle of a current image plane may be adapted to the detected motion direction so that the image plane is continuously aligned to the motion direction independently of the position of the ultrasound probe.

Hence, a continuous three-dimensional ultrasound data stream can be received in real time and the image plane in which the two-dimensional image data is displayed can be determined correspondingly in real time so that an optimal view of the dynamic behavior of an object or an organ of the patient can be provided.

Consequently, the present invention achieves an improved visualization of the dynamic behavior which is automatically aligned and therefore less complicated for the user.

In a preferred embodiment, the motion detection unit comprises a motion estimation unit for estimating the motion of the object on the basis of the three-dimensional ultrasound data stream. This is a possibility to determine a motion in the three-dimensional ultrasound data with low calculation effort and in real time corresponding to the data stream of the three-dimensional ultrasound data.

In a preferred embodiment, the motion detection unit is adapted to determine the motion on the basis of consecutive time frames of the three-dimensional ultrasound data stream. This is a possibility to determine the motion on the basis of the three-dimensional ultrasound data with high reliability.

In a preferred embodiment, the motion detection unit is adapted to determine the motion on the basis of pattern detection within the consecutive time frames. This is a possibility to determine the motion with low technical effort on the basis of pattern matching.

In a preferred embodiment, the motion detection unit is adapted to estimate a three-dimensional translation motion between consecutive time frames on the basis of the motion determined in the consecutive data frames. This is a possibility to extract a relevant dynamic behavior of an object of the patient on the basis of a global motion in the three-dimensional ultrasound data so that the dynamic behavior of the object can be determined with high precision.

In a preferred embodiment, the spatial rotation angle is determined on the basis of the translation motion. This is a possibility to determine the spatial rotation angle with high precision on the basis of the translation motion which is determined on the basis of the general motion in the three-dimensional ultrasound data.

In a preferred embodiment, the motion detection unit is adapted to determine a motion vector on the basis of an average of a plurality of consecutive translation motions. This is a possibility to achieve a smooth adaption and a continuous change of the image plane.

In a preferred embodiment, the image processing unit is adapted to determine the spatial rotation angle of the image plane such that a motion vector of the determined motion and the image plane are in-plane. Hence, the image plane depicts an in-plane motion. This is a possibility to improve the visualization of the dynamic behavior, since a motion in-plane with the image plane can be visualized in a two-dimensional image plane with high precision.

In a preferred embodiment, the image processing unit is adapted to determine a second image plane inclined to the image plane, wherein a motion vector of the determined motion is in-plane with the second image plane and wherein the image processing unit is adapted to determining additional two-dimensional ultrasound image data on the basis of the three-dimensional ultrasound data in the second image plane. The so determined additional two-dimensional ultrasound image data can be displayed in addition to the image data of the first image plane. This is a possibility to align the second image plane to the motion so that the motion can be displayed in-plane of the second image plane.

In a preferred embodiment, the image processing unit is designed to adapt the spatial rotation angle of the image plane on the basis of the determined motion. This is a possibility to continuously adapt the image plane to the current motion so that a two-dimensional image aligned to the detected motion can be provided in real time.

In a preferred embodiment, the output interface is adapted to provide the two-dimensional image data to the display unit as a continuous data stream. This is a possibility to display the two-dimensional images in real time corresponding to the captured three-dimensional image data.

In a preferred embodiment, the ultrasound imaging apparatus further comprises a user interface which is adapted to enable and disable the alignment of the ultrasound image data to the determined direction of the motion. This is a possibility to activate and deactivate the image plane adaption and the motion steering of the ultrasound imaging apparatus.

As mentioned above, the present invention provides the possibility to automatically adjust the image plane and the two-dimensional ultrasound images to the motion detected in the three-dimensional ultrasound data so that an improved visualization of dynamic behavior of organs or objects of the patient can be provided. Further, since the motion is determined automatically, the dynamic behavior can be located and displayed accordingly with low handling effort which is therefore comfortable for the user. Since the image plane is adapted to the motion detected in the ultrasound data, the dynamic behavior can be displayed nearly independently of the viewing direction of the ultrasound probe, so that the alignment of the image planes to the motion can be provided nearly independently of the orientation of the probe.

Consequently, an optimal alignment of the image planes can be provided with low handling effort so that the use of the ultrasound imaging apparatus is comfortable for the user.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
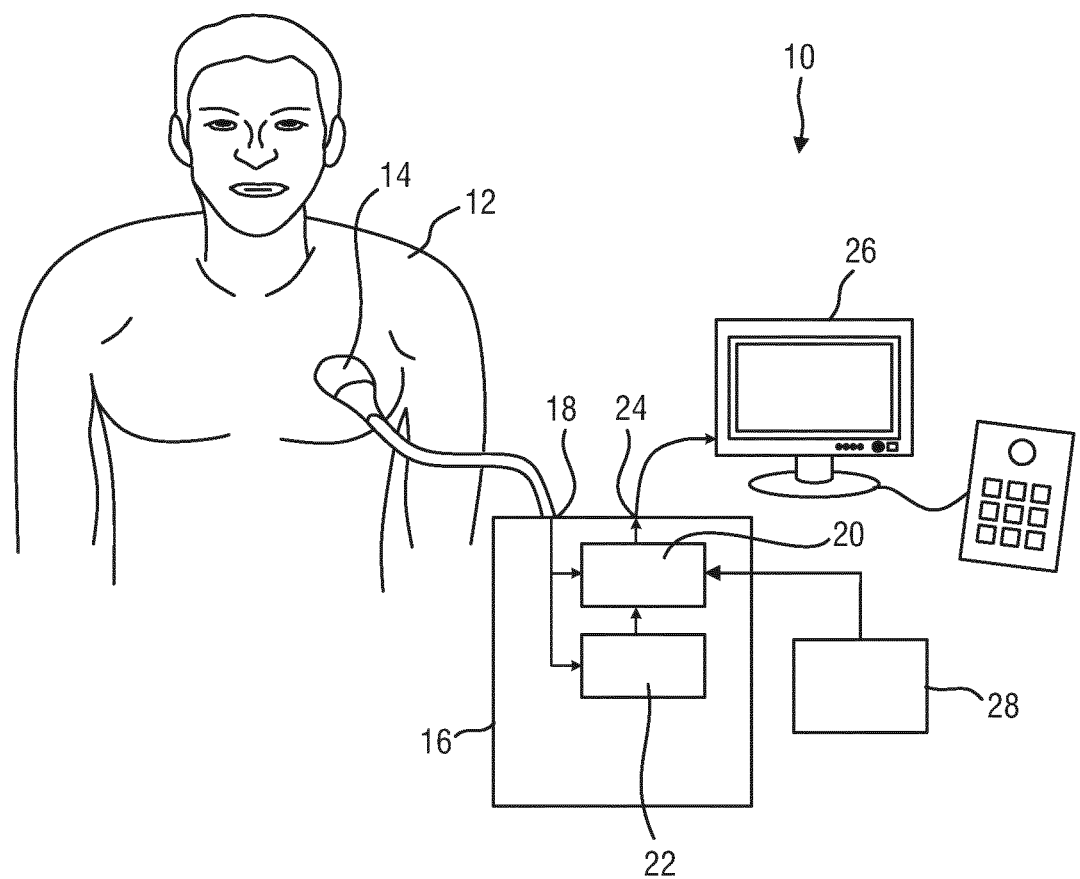
FIG. 1 shows a schematic representation of an ultrasound imaging apparatus in use to scan a volume of a patient's body.

FIG. 1 shows a schematic illustration of an ultrasound imaging system generally denoted by 10. The ultrasound imaging system 10 is applied to inspect a volume of an anatomical side, in particular an anatomical side of a patient 12. The medical imaging apparatus 10 comprises an ultrasound probe 14 having at least one transducer array including a multitude of transducer elements for transmitting receiving ultrasound waves. The transducer elements are preferably arranged in a two-dimensional array for providing three-dimensional ultrasound data.

The ultrasound imaging system 10 comprises in general an ultrasound imaging apparatus 16 connected to the ultrasound probe 14 for evaluating the three-dimensional ultrasound data received from the ultrasound probe 14 and for determining and providing two-dimensional ultrasound images of the patient 12. The ultrasound imaging apparatus 16 comprises an input interface 18 for receiving three-dimensional ultrasound data from the ultrasound probe 14. The input interface 18 is adapted to receive the three-dimensional ultrasound data in real time in a continuous data stream so that a real time or a live ultrasound imaging is possible.

The ultrasound imaging apparatus 16 comprises an image processing unit 20 connected to the input interface 18 for receiving the three-dimensional ultrasound data and for providing two-dimensional ultrasound image data from the volume or the object of the patient 12 determined on the basis of the three-dimensional ultrasound image data received from the ultrasound probe 14.

The ultrasound imaging apparatus 16 further comprises a motion detection unit 22 connected to the input interface 18 for receiving the three-dimensional ultrasound data from the ultrasound probe 14 and for determining a motion of an object in the three-dimensional ultrasound data and, further, a direction of the motion in the three-dimensional ultrasound data. The motion detection unit 22 is connected to the image processing unit 20 and provides the direction of the motion detected in the three-dimensional ultrasound data to the image processing unit 20.

The image processing unit 20 receives the spatial direction of the motion from the motion detection unit 22 and determines an image plane corresponding to the spatial direction of the motion within the volume of the patient 12. The image processing unit 20 determines two-dimensional ultrasound image data on the basis of the three-dimensional ultrasound data in the image plane and provides the so determined two-dimensional ultrasound image data to an output interface 24 of the ultrasound imaging apparatus 16. The output interface 24 is connected to a display unit 26 for displaying the two-dimensional ultrasound image data received from the ultrasound imaging apparatus 16. The image processing unit 20 may further determine an additional second image plane inclined to the image plane and may further determine an additional third image plane inclined to the image plane and inclined to the second image plane and to display the respective two-dimensional ultrasound image data in the additional image planes on the display unit 26.

The image plane of the two-dimensional ultrasound image data is adapted to the motion direction determined in the three-dimensional ultrasound data so that dynamic processes in the volume inspected by the ultrasound probe 14 can be visualized in the two-dimensional ultrasound image data and displayed on the display 26. The two-dimensional ultrasound image data is provided as a continuous data stream corresponding to the continuous data stream of the three-dimensional ultrasound data received from the ultrasound probe 14 so that two-dimensional live images can be displayed on the display unit 26, wherein the image planes are respectively adapted to the motion of the three-dimensional ultrasound data. Preferably, a motion vector of the motion in the three-dimensional ultrasound data is determined and a spatial rotation angle of the image plane is determined such that the motion direction is in-plane with the image plane.

The additional second image plane may also be adapted to the motion direction determined in the three-dimensional ultrasound data so that the motion vector is arranged in-plane in the second image plane and dynamic processes in the volume inspected by the ultrasound probe 14 can be visualized in the additional two-dimensional ultrasound image data displayed on the display 26 in addition to the first image plane. The image plane and the additional second image plane may be arranged so that the motion vector is an intersection of the two image planes. Hence, the motion can be arranged or displayed in-plane in the two image planes. The additional third image plane is arranged inclined to the image plane and the second image plane and preferably orthogonally to the image plane and the second image plane so that the motion vector is out-of-plane of the third image plane. The third image plane can be displayed on the display 26 in order to display most of the out-of-plane motion.

The motion in the three-dimensional ultrasound data is continuously determined and the spatial rotation angle(s) of the image plane is continuously adapted to the currently detected motion so that the two-dimensional ultrasound image data is displayed continuously corresponding to the motion detected in the three-dimensional ultrasound data. Hence, the two-dimensional images displayed by the display unit 26 are continuously aligned to the detected motion and can be provided as a live image in real time.

The motion detection unit 22 receives the continuous data stream of the three-dimensional ultrasound data and determines the motion vector on the basis of consecutive time frames of the ultrasound image data by detecting corresponding pattern in the ultrasound data so that the motion can be determined on the basis of pattern matching.

The motion detection unit 22 comprises a motion estimation unit for estimating a translation motion, e.g. by pattern matching or image value matching, on the basis of which the image planes are determined. For each new incoming ultrasound data frame, a three-dimensional translation is estimated between the new incoming frame and the previous data frame. The translation motion is a three-dimensional vector between corresponding positions or features of two of the 3D ultrasound data frames. The translation motion is stored in an array. On the basis of the array of translation motions a mean three-dimensional translation is calculated which considers a predefined amount of N values of the translation motion. The direction of the mean translation motion, which is preferably determined as a motion vector determines the value of the spatial rotation angle of the image plane. If the image plane is correspondingly determined and the two-dimensional ultrasound image data is determined in this image plane, the motion and the two-dimensional image are in-plane, so that the dynamic behavior can be visualized on the two-dimensional display screen. For an amount of N=1, the spatial rotation angle strictly follows the instantaneous value of the translation motion. In order to provide a smooth two-dimensional ultrasound image displayed on the display unit 26 the value of N is preferably larger than 1. By means of this, the spatial rotation angle is continuously and smoothly updated corresponding to the pace of the incoming time frames of the three-dimensional ultrasound data stream.

The ultrasound imaging system 10 may be provided for multimodal imaging, wherein the ultrasound image data can be combined with medical images received from a database 28 or another medical imaging system 28 like computer tomography or magnetic resonance tomography connected to the image processing unit 20.

Figure 2:
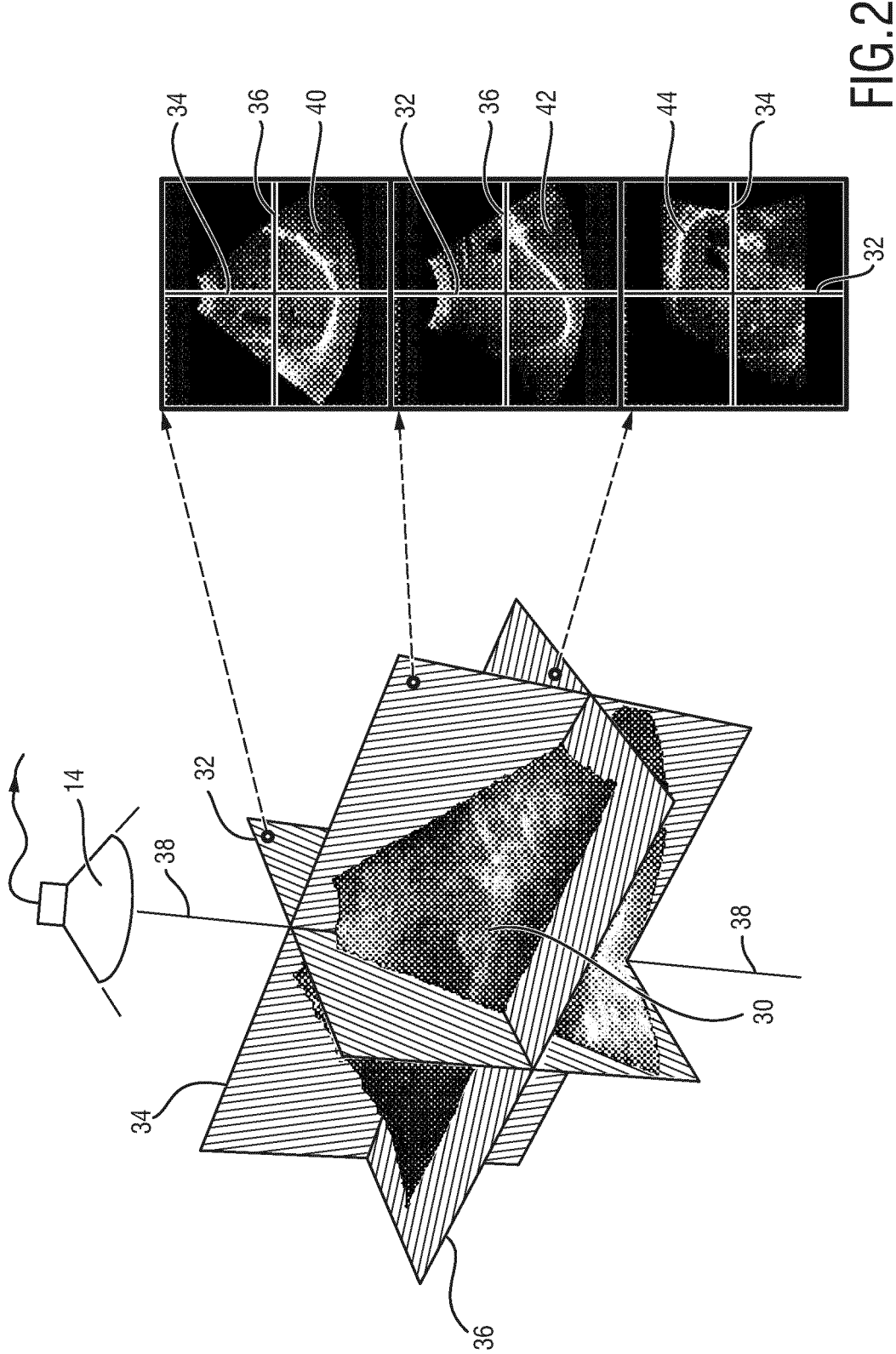
FIG. 2 shows a perspective illustration of three-dimensional ultrasound image data and three image planes in the ultrasound data.

FIG. 2 shows a perspective illustration of a field of view of the ultrasound probe 14. In the field of view, which is generally denoted by 30, three image planes 32, 34, 36 are defined, which are in this embodiment disposed or arranged orthogonally to each other. Two of the image planes 32, 34 are disposed parallel to a viewing direction 38 of the ultrasound probe 14 and one of the image planes 36 is disposed orthogonally to the viewing direction 38. On the basis of these image planes, three two-dimensional ultrasound images 40, 42, 44 are determined as shown in FIG. 2. The corresponding other image planes 32, 34, 36 are respectively indicated in the two-dimensional ultrasound images 40, 42, 44.

Figure 3:
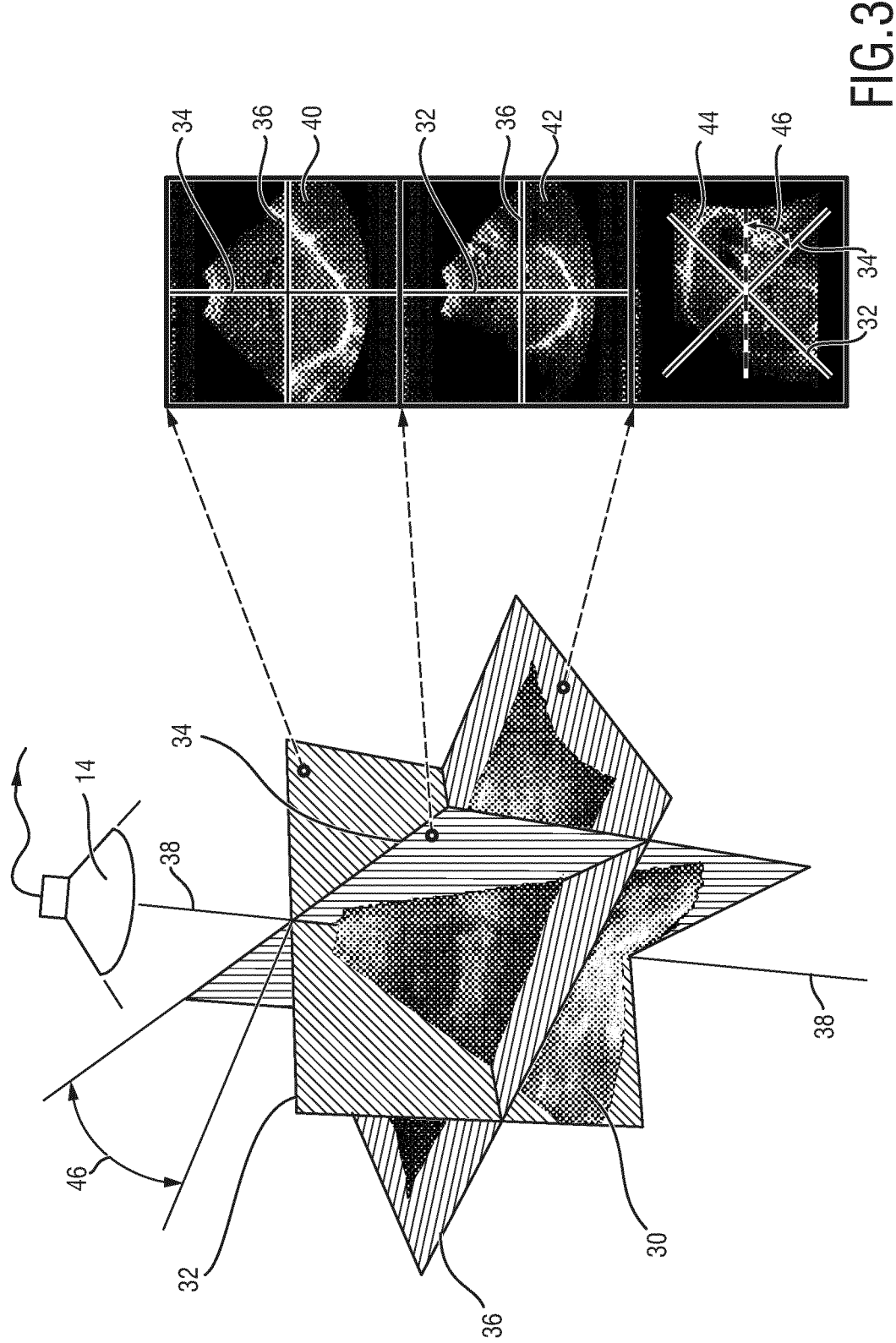
FIG. 3 shows a perspective view of an adaptation of the image planes in the three-dimensional ultrasound data to a detected motion.

In FIG. 3 a further perspective view of the field of view 30 is shown including the image planes adapted to a motion determined in the three-dimensional ultrasound image data. Identical elements are denoted by identical reference numerals, wherein here merely the differences are explained in detail.

The vertical image planes 32, 34 are turned around a vertical axis corresponding to the viewing direction 38 by a spatial rotation angle 46, which is determined on the basis of or corresponding to the motion vector determined in the three-dimensional ultrasound image data. In this embodiment, the two image planes 32, 34 are turned around by the spatial rotation angle 46 and are maintained to be arranged orthogonally to each other. The vertical image planes 32, 34 are spatially rotated or displaced on the basis of one motion vector so that the motion direction becomes 'in-plane' with respect to one of the image planes.

The image planes 32, 34, 36 may also be rotated around an axis, which is inclined to the viewing direction 38 of the probe 14. In other words, the spatial rotation angle may be directed in any spatial direction, so that any motion can be visualized in the two-dimensional images.

The image planes 32, 34, 36 may also be rotated in a first step around the vertical axis in order to arrange the motion direction to be in-plane with the image plane 32 and in a second step the image planes 32, 34, 36 may also be rotated within the image plane 32 i.e. around a line of intersection between the image planes 32 and 34 in order to arrange the motion direction to be in-plane with the image plane 36.

Hence, the image planes and the corresponding two-dimensional images 40, 42, 44 can be adapted to the motion of an object in the field of view 30 so that the dynamic behavior of the object can be visualized optimally in the two-dimensional ultrasound images 40, 42, 44.

Figure 4:
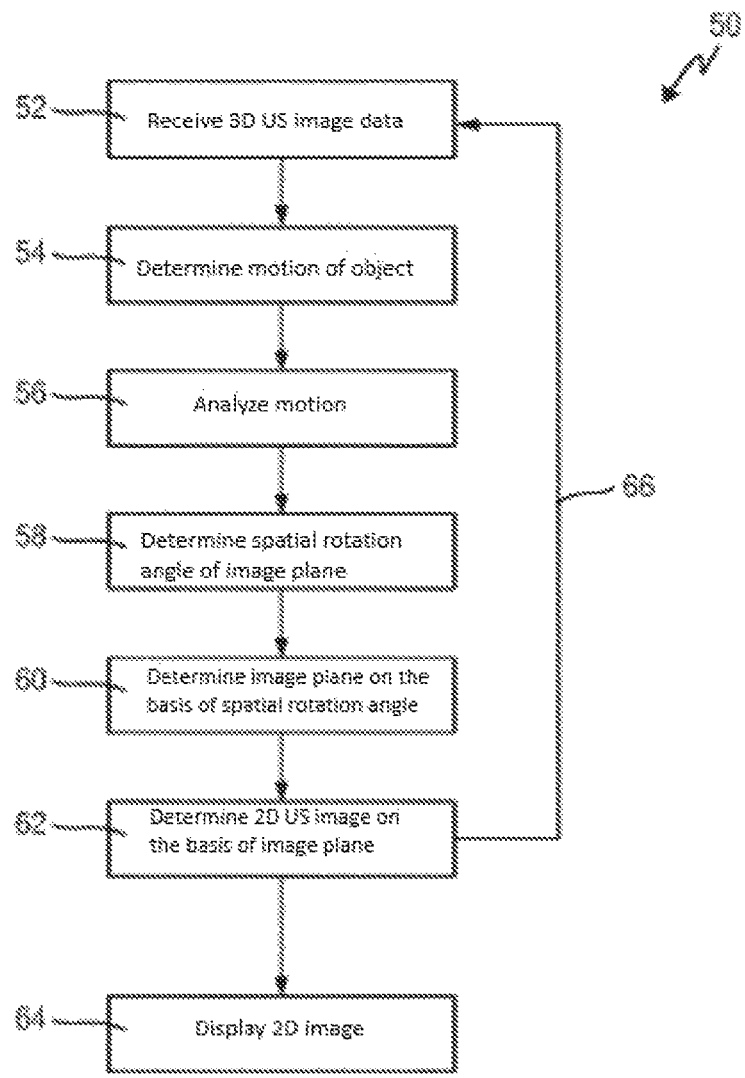
FIG. 4 shows a schematic flow diagram of a method for providing two-dimensional ultrasound images of a patient.

FIG. 4 shows a schematic flow diagram of a method for evaluating ultrasound image data and for providing two-dimensional ultrasound images of a patient. The method shown in FIG. 4 is generally denoted by 50.

The method 50 starts with receiving three-dimensional ultrasound image data from the ultrasound probe 14 at the input interface 18 as shown at 52. The motion of the object within the three-dimensional ultrasound image data is determined at step 54 and the motion is analyzed at step 56 in order to estimate a general motion and to determine a direction of the motion in the three-dimensional ultrasound image data. At a step 58, the spatial rotation angle 46 of the image plane 32, 34 is determined corresponding to the direction of the motion determined at step 56.

At step 60, the image plane 32, 34 is determined on the basis of the spatial rotation angle and at step 62, the two-dimensional ultrasound images 40, 42, 44 are determined on the basis of the correspondingly determined image planes 32, 34. At step 64, the two-dimensional image data is provided to the display unit 26 in order to display the two-dimensional images 40, 42, 44.

The method 50 is a continuous process which is performed corresponding to the continuous data stream and applied to the consecutive data frames received from the ultrasound probe 14 as indicated by a loop 66 shown in FIG. 4.

Hence, the two-dimensional ultrasound images 40, 42, 44 can be provided aligned to the motion of the object in the field of view 30 in real time corresponding to the continuous data stream received from the ultrasound probe 14.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. An ultrasound imaging apparatus for providing two-dimensional ultrasound images of a patient, the ultrasound imaging apparatus comprising a processor configured to:
   receive three-dimensional ultrasound data of a volume of the patient as a continuous data stream;
   provide two-dimensional ultrasound image data of an object in the three-dimensional ultrasound data to a display, wherein the two-dimensional ultrasound image data of the object is in an image plane within the volume;
   determine a motion of the object in the three-dimensional ultrasound data and a direction of the motion of the object in the three-dimensional ultrasound data;
   determine a spatial rotation angle of the image plane within the volume on a basis of the direction of the motion determined in the three-dimensional ultrasound data for spatially orienting an altered image plane;
   determine, based at least in part, on a rotation of the image plane based on the spatial rotation angle, the altered image plane within the volume that is spatially oriented relative to the image plane such that the direction of the motion of the object is in-plane with the altered image plane, wherein the altered image plane depicts the in-plane motion of the object; and
   provide two-dimensional ultrasound image data in the altered image plane to the display.

2. An ultrasound imaging apparatus as claimed in claim 1, wherein the processor is configured to determine the motion of the object by estimating the motion of the object from the three-dimensional ultrasound data in the continuous data stream.

3. An ultrasound imaging apparatus as claimed in claim 1, wherein the processor is configured to determine the motion of the object from consecutive time frames of the three-dimensional ultrasound data in the continuous data stream.

4. An ultrasound imaging apparatus as claimed in claim 3, wherein the processor is configured to determine the motion of the object using pattern detection within the consecutive time frames.

5. An ultrasound imaging apparatus as claimed in claim 3, wherein the processor is further configured to estimate a three-dimensional translation motion between consecutive time frames based on the motion determined in the consecutive data frames.

6. An ultrasound imaging apparatus as claimed in claim 5, wherein the processor is configured to determine the spatial rotation angle for spatially orienting the altered image plane based on the translation motion.

7. An ultrasound imaging apparatus as claimed in claim 3, wherein the processor is configured to determine a motion vector that represents the direction of the motion by averaging a plurality of consecutive translation motions.

8. An ultrasound imaging apparatus as claimed in claim 1, wherein the image plane is a first image plane and wherein the processor is further configured to determine a second image plane inclined to the first image plane such that the direction of the motion is aligned with an intersection of the first and second image planes.

9. An ultrasound imaging apparatus as claimed in claim 1, wherein the processor is configured to determine and provide to the display, as a continuous data stream, two-dimensional ultrasound image data in successive altered image planes successively spatially oriented to maintain the direction of motion in-plane with a respective one of the successive altered image planes.

10. An ultrasound imaging apparatus as claimed in claim 1, further comprising a user interface which is adapted to enable and disable an alignment of the two-dimensional ultrasound image data to the determined direction of the motion.

11. An ultrasound imaging system, comprising:
the ultrasound imaging apparatus of claim 1,
an ultrasound acquisition unit including an ultrasound probe for acquiring the three-dimensional ultrasound data, and
the display for displaying ultrasound images generated from the three-dimensional ultrasound data.

12. An ultrasound image evaluation method for providing two-dimensional ultrasound images of a patient, comprising the steps of:
receiving three-dimensional ultrasound data of a volume of the patient as a continuous data stream;
providing two-dimensional ultrasound image data of an object in the three-dimensional ultrasound data to a display, wherein the two-dimensional ultrasound image data of the object is in an image plane within the volume;
determining a motion of the object within the three-dimensional ultrasound data and a direction of the motion of the object in the three-dimensional ultrasound data;
determining a spatial rotation angle of the image plane within the volume on a basis of the direction of the motion determined in the three-dimensional ultrasound data for spatially orienting an altered image plane;
determining, based at least in part, on a rotation of the image plane based on the spatial rotation angle, the altered image plane within the volume that is spatially oriented relative to the image plane such that the direction of the motion of the object is in-plane with the altered image plane, wherein the altered image plane depicts the in-plane motion of the object; and
providing two-dimensional ultrasound image data in the altered image plane to the display.

13. A non-transitory computer readable medium comprising instructions for causing a computer to execute the steps of the method as claimed in claim 12, when said instructions are carried out on the computer.

* * * * *